US010864136B2

(12) United States Patent
Garteiser et al.

(10) Patent No.: US 10,864,136 B2
(45) Date of Patent: Dec. 15, 2020

(54) MEDICAL APPARATUS FOR TREATING CELLS WITH VIBRATIONS

(71) Applicants: KONINKLIJKE PHILIPS N.V., Eindhoven (NL); INSTITUT NATIONAL DE LA SANTE DE LA RECHERCHE MEDICALE (INSERM), Paris (FR)

(72) Inventors: Philippe Francois Thierry Garteiser, Asnieres sur Seine (FR); Leon Christiaan Terbeek, Veldhoven (NL); Ralph Roman Sinkus, Parmain (FR); Sabrina Nicole Dolorès Doblas, Asnières sur Seine (FR); Simon Auguste Lambert, Paris (FR); Valérie Paradis, Suresnes (FR)

(73) Assignees: KONINKLIJKE PHILIPS N.V., Eindhoven (NL); INSTITUT NATIONAL DE LA SANTE DE LA RECHERCHE MEDICALE, Paris (FR)

( * ) Notice: Subject to any disclaimer, the term of this patent is extended or adjusted under 35 U.S.C. 154(b) by 1303 days.

(21) Appl. No.: 15/023,710

(22) PCT Filed: Sep. 23, 2014

(86) PCT No.: PCT/EP2014/070175
§ 371 (c)(1),
(2) Date: Mar. 22, 2016

(87) PCT Pub. No.: WO2015/040230
PCT Pub. Date: Mar. 26, 2015

(65) Prior Publication Data
US 2016/0228324 A1    Aug. 11, 2016

(30) Foreign Application Priority Data

Sep. 23, 2013    (EP) .................................. 13306292

(51) Int. Cl.
A61H 23/00       (2006.01)
A61H 23/02       (2006.01)
(Continued)

(52) U.S. Cl.
CPC ......... *A61H 23/0218* (2013.01); *A61B 5/055* (2013.01); *A61H 23/02* (2013.01);
(Continued)

(58) Field of Classification Search
CPC .................................................. A61H 23/0218
See application file for complete search history.

(56) References Cited

U.S. PATENT DOCUMENTS

2004/0122323 A1    6/2004    Vortman

FOREIGN PATENT DOCUMENTS

EP    1720028    11/2006
EP    1721594    11/2006
(Continued)

OTHER PUBLICATIONS

Ingber, "Cellular mechanotransduction: putting all the pieces together again", FASEB Journal, vol. 20, No. 7, 811-827.
(Continued)

*Primary Examiner* — Joseph M Santos Rodriguez
(74) *Attorney, Agent, or Firm* — Sherry Austin

(57) ABSTRACT

The invention provides for a medical apparatus (100, 200, 300) for treating cells of a subject comprising at least one transducer (102, 224) with a vibrating surface (116). The transducer further comprises an applicator (118, 600) for attaching the vibrating surface to an outer surface of the subject (108, 218). The transducer is operable to vibrate at a frequency between 10 Hz and 1000 Hz. The medical apparatus further comprises a controller (104, 222, 230) for controlling the vibration of the transducer. The controller is operable for causing the transducer to vibrate for greater
(Continued)

than a predetermined period of time for treating the cells. The predetermined period of time is greater than one hour.

18 Claims, 7 Drawing Sheets

(51) Int. Cl.
*A61H 23/04* (2006.01)
*A61B 5/055* (2006.01)

(52) U.S. Cl.
CPC ....... *A61H 23/04* (2013.01); *A61H 2201/165* (2013.01); *A61H 2201/5033* (2013.01); *A61H 2230/00* (2013.01)

(56) References Cited

FOREIGN PATENT DOCUMENTS

| | | |
|---|---|---|
| JP | 2000225161 A | 8/2000 |
| JP | 2009297408 | 12/2009 |
| JP | 2013006116 | 1/2013 |
| WO | 2010/093753 | 8/2010 |
| WO | 2012/116038 | 8/2012 |

OTHER PUBLICATIONS

Ehman, et al., "Vibration safety limits for magnetic resonance elastography", Phys. Med. Biol. 2008, 54(3): 925:935.
Philippe Garteiser et al: "Abstract 3345: Induction of apoptosis by high levels of oscillatory shear strain: proof of concept in a human colon cancer metastasis cell line.—Garteiser et al,—Cancer Research", Proceedings of the 104th the American Association Research; Apr. 6-10, 2013.

MEDICAL APPARATUS FOR TREATING CELLS WITH VIBRATIONS

CROSS REFERENCE TO RELATED APPLICATIONS

This application is the U.S. National Phase application under 35 U.S.C. § 371 of International Application No. PCT/EP2014/070175, filed Sep. 23, 2014, published as WO 2015/040230 on Mar. 26, 2015, which claims the benefit of European Patent Application Number 13306292.7 filed Sep. 23, 2013. These applications are hereby incorporated by reference herein.

TECHNICAL FIELD

The invention relates to apparatuses for internally vibrating a subject, in particular to methods and apparatuses for inducing mechanotransduction effects in cells.

BACKGROUND OF THE INVENTION

Cells of many types are able to sense the mechanical status of their microenvironment by a range of processes grouped under the term "mechanotransduction." One of the known effects caused by mechanotransduction is programmed cell death, or apoptosis. The journal article Ingber, "Cellular mechanotransduction: putting all the pieces together again," FASEB Journal, vol. 20 no. 7 811-827, doi: 10.1096/fj.05-5424rev provides a review of mechanotransduction.

The journal article Ehman et. al. "Vibration safety limits for magnetic resonance elastography" Phys. Med. Biol. 2008, 54(3): 925-935 describes a study of the magnitude of vibrations caused by magnetic resonance elastography to make a comparison to a European Union directive regarding limits to whole body and extremity accelerations due to vibrations.

The abstract: '*Induction of apoptosis by high levels of oscillatory shear* strain: *proof of concept in a human colon cancer metastasis cell line*', by Ph. Garteiser et al. in the Proc. of the $104^{th}$ annual meeting of the American Association for Cancer Research 73(2103)3345 discloses a proof of concept of the theoretical possibility to selectively induce cell death by low frequency oscillatory strain.

SUMMARY OF THE INVENTION

The invention provides for a medical apparatus, a computer program product and a method in the independent claims. Embodiments are given in the dependent claims. As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a medical apparatus for treating cells of a subject. The medical apparatus comprises at least one transducer with a vibrating surface. The transducer further comprises an applicator for attaching the vibrating surface to an outer surface of the subject. The applicator may for instance be an adhesive or band or strap for attaching the transducer to the outer surface of the subject. The transducer is operable to vibrate at a frequency between 10 Hz and 1000 Hz. In some instances the transducer may have a variable frequency of some range between 10 Hz and 1000 Hz. In other examples the transducer may be operable to operate at one or more fixed frequencies between 10 Hz and 1000 Hz. The medical apparatus further comprises a controller for controlling the vibration of the transducer.

The controller is operable for causing the transducer to vibrate for greater than a predetermined period of time. The predetermined period of time is greater than one hour for treating the cells. In some examples the cells could be cancer cells. In some instances treating the cells may result in cell death. Exposing cells to low frequency, low intensity and long duration shear waves may induce cell death by apoptosis. In general cells of many types are able to sense mechanical status of their micro-environment by a range of processes grouped under the term mechanotransduction. One known effect caused by mechanotransduction is a programmed cell death or apoptosis. This may have a variety of uses. One would be the treatment of cancer cells to kill them through the process of apoptosis.

In this embodiment the predetermined time is determined to be greater than one hour. The predetermined period of time may be broken into a number of sub-chunks of time or intervals such that the bind duration is the predetermined of time. If there are pauses of time that are on the same order as the predetermined period of time then the mechanotransduction process induced in the cells is unchanged. In one example treating the cells may refer to causing or inducing apoptosis in the cells. In another example the term 'treating cells' may refer to causing a mechanotransduction effect in the cells.

In one example the vibrating surface for each of the transducers is less than 42 cm.

In one example the transducer is vibrated such that it generates a shear strain value of at least 0.1% within a portion of the subject.

In another embodiment the at least one transducer is multiple transducers. The controller is operable for controlling the vibrational phase and/or the amplitude of each of the multiple transducers. The controller comprises a processor. The medical apparatus further comprises a magnetic resonance imaging system for measuring magnetic resonance data from the subject within an imaging zone. The multiple transducers are operable to be placed within the imaging zone. During operation they are placed within the imaging zone or adjacent to the imaging zone such that the regions of the subject vibrated by the multiple transducers are within the imaging zone. The medical apparatus further comprises a memory for storing machine-executable instructions and a first pulse sequence.

A pulse sequence as used herein is a specification or instructions on how to operate a magnetic resonance imaging system to acquire magnetic resonance data. The use of a particular pulse sequence determines the method for which the magnetic resonance data is acquired. The first pulse sequence is a motion sensitive pulse sequence. A motion sensitive pulse sequence as used herein encompasses a pulse sequence that is able to detect the motion of the subject internally. Examples of a motion sensitive pulse sequence are pulse sequences that perform flow encoding, that are able to measure diffusion, and elastographic pulse sequences. In magnetic resonance elastography the local shear strain can be measured in addition to the stiffness of the subject's tissue. The combination of magnetic resonance elastography and the application of shear waves using multiple transducers enables to actually measure the local degree of induced shear forces and properly steer the therapy.

Execution of the machine-executable instructions causes the processor to receive target data descriptive of a location of a target zone within the subject. For instance the target data may be contained within a treatment plan or may be entered into a user interface by a physician or operator of the medical apparatus. Execution of the instructions further causes the processor to individually vibrate each of the multiple transducers using the controller. Execution of the instructions further causes the processor to acquire first magnetic resonance data during the vibration of each of the multiple transducers using the first pulse sequence. First magnetic resonance data as used here encompasses magnetic resonance data. That is to say the processor uses the pulse sequence to control the magnetic resonance imaging system to acquire the first magnetic resonance data.

Execution of the instructions further causes the processor to calculate a vibration map for each of the multiple transducers using the first magnetic resonance data. The vibration map is descriptive of the shear strain value of vibrations within the subject caused by each of the multiple transducers. The multiple transducers are on the surface of the subject.

The vibration map may also be descriptive of the phase of vibrations caused by each of the multiple transducers within the subject. Execution of the instructions further causes the processor to calculate transducer control data to control the multiple transducers to cause a shear strain value of at least a first predetermined value within at least part of the target zone and less than a second predetermined value outside of the target zone using the vibration map for each of the multiple transducers.

Execution of the instructions further causes the processor to control the multiple transducers with the transducer control data using the controller. In this embodiment the phase and the shear strain value of individual transducers or groups of transducers is measured. Once these vibration maps are acquired it is straight forward to modify the amplitude and/or phase of vibrations caused by the multiple transducers such that the shear strain value within the target zone is above the first predetermined value and the shear strain value outside of the target zone is below a second predetermined value. This may be advantageous because it enables the causing of mechanotransduction effects for cells within the target zone while leaving cells outside of the target zone unaffected.

In one example the first predetermined value is 0.1% or larger. In another example the second predetermined value is 0.05% or less. In another example the frequency is preferably between 20-200 Hz. In one example the frequency of all of the multiple transducers is the same. In another example the frequency of the multiple transducers is also controllable. For instance the frequency applied to the transducers may be used to control how deeply the shear waves propagate into the body of a subject. By choosing an appropriate vibration frequency it may also help to control the location of the target zone.

In another embodiment execution of the machine-executable instructions further causes the processor to acquire further magnetic resonance data during control of the multiple transducers with the transducer control data using the magnetic resonance imaging system. The acquisition of the further magnetic resonance data is performed using the first pulse sequence. Further magnetic resonance data as used here encompasses magnetic resonance data. Execution of the instructions further causes the processor to calculate a further vibration map using the further magnetic resonance data. Execution of the instructions further causes the processor to halt vibration of the multiple transducers if the shear strain value is not at least above the first predetermined value within at least part of the target zone and/or is greater than the second predetermined value outside the target zone.

The application of the long duration shear waves by the transducers is performed for a long time predetermined period. During this time it is possible to make further magnetic resonance measurements to ensure that the shear strain value induced by the multiple transducers is sufficiently high in the target zone to induce a mechanotransduction effect and sufficiently low outside of the target zone to avoid inducing a mechanotransduction effect. This may be performed in several ways. For instance it may be performed immediately after starting the control of the multiple transducers using the controller or it may also be performed repeatedly during the control of the multiple transducers with the transducer control data. For instance a subject may move or have internal motion which shifts the position of the vibrations caused by each of the multiple transducers within the subject. This example may also involve modifying the transducer control data to correct for internal or external motion of the subject. This embodiment may be beneficial because it more accurately ensures that the shear strain value is above the first predetermined value in the target zone and less than the second predetermined value outside of the target zone.

In another embodiment the memory stores a second pulse sequence. The second pulse sequence is a pulse sequence operable for acquiring magnetic resonance imaging data. The second pulse sequence is an imaging pulse sequence. Execution of the machine-executable instructions further causes the processor to acquire image magnetic resonance data of the subject using the magnetic resonance imaging system. This is performed using the second pulse sequence. Image magnetic resonance data as used herein encompasses magnetic resonance data. Execution of the machine-executable instructions further causes the processor to reconstruct an image using the image magnetic resonance data. Execution of the instructions further causes the processor to locate the target zone within the image using an image recognition module. The step of locating the target zone within the image using the image recognition module registers the target data to the medical apparatus. This may enable more accurate targeting of the target zone.

In another embodiment the controller is operable for adjusting the vibration frequency of each of the multiple transducers. Execution of the instructions further causes the processor to repeat the individual vibration of each of the multiple transducers using the controller and acquisition of the multiple transducer frequencies. The vibration map is a multi-frequency vibration map. Calculating the transducer control data comprises selecting the frequency for the multiple transducers. As was mentioned above, the frequency effects the propagation of vibrations within a subject. Adjusting the vibration frequency of the multiple transducers may allow more accurate targeting of the target zone.

In another embodiment the controller is operable for adjusting the vibrational amplitude and phase of each of the multiple transducers. Calculating the transducer control data comprises selecting a vibrational amplitude and phase for each of the multiple transducers. This embodiment again may enable more accurate targeting of the target zone.

In another embodiment the magnetic resonance imaging system comprises a magnet for generating a main magnetic field. The multiple transducers are operable for functioning within and outside of the main magnetic field. This embodiment may be beneficial because it may enable the image to be removed from the magnetic resonance imaging system. This for instance may be advantageous because it may be uneconomical for a hospital to leave a subject within a magnetic resonance imaging system for a period of several hours. Removing the subject enables a higher throughput. A subject could be placed in a magnetic resonance imaging system to determine the transducer control data and then removed once the vibration map is determined. In another example the subject is removed after the further vibration map is determined.

The transducers may for example exploit pneumatic technology. This may be very useful provided the amplitude and phase are controlled to roughly 1%. Piezoelectric technology may also be provided that the amplitude and phase are controlled within approximately 1% over the claimed operating range in terms of amplitude and frequency. This may enable the transducers to operate within magnetic fields and also outside of magnetic fields.

In another embodiment the medical instrument comprises a subject support. The subject support is operable for removing the subject, the controller and the multiple transducers from the magnetic resonance imaging system during the predetermined period of time. This is to say that once the transducer control data has been determined it is possible to remove the subject from the magnetic resonance imaging system to enable other subjects to be placed into the same magnetic resonance imaging system during the control of the multiple transducers with the transducer control data using the controller.

In another embodiment the multiple transducers are electromagnetically driven transducers. Electromagnetically driven transducers as used herein encompass transducers which have a coil that interacts with the magnetic field of a magnetic resonance imaging system to provide for actuation or the vibration of the vibrating surface.

In another embodiment the first predetermined value is greater than or equal to any one of the following: 0.1%, 1%, 2% and 5%.

In another embodiment the second predetermined value is less than or equal to 0.5%.

In another embodiment the at least one transducer is a single transducer. The applicator is operable for attaching the vibrating surface to skin. The vibrating surface has a surface area less than 0.25 cm$^2$. This embodiment may be beneficial because it may enable a dermatologist, general practitioner or other healthcare provider to effectively treat cells on the skin of a subject or within the skin. For instance a melanoma may be visible to the eye. The healthcare provider may be able to place the single transducer over the desired cells or melanoma and effectively treat the cells within a normal office without the need of any imaging equipment.

In another embodiment the frequency is between 200 and 1000 Hz. This frequency range may be beneficial because the vibrations will be attenuated within the skin of the subject. In one embodiment the healthcare provider can make an estimate of how he or she would like to treat the cells and then adjust the frequency accordingly. In such a case the controller may have a control for adjusting the frequency. In another example the multiple transducer has a transparent portion. This for instance may enable the healthcare provider to put an alignment mark on the skin or outer surface of the subject. The transparent or other aligning object of the single transducer then can be accurately aligned with the subject.

In another embodiment the predetermined period of time is any one of the following: greater than 1.5 hours, greater than 2 hours, greater than 2.5 hours, greater than 3 hours, greater than 3.5 hours, and greater than 4 hours.

In another aspect the invention provides for a computer program product comprising machine-executable instructions for execution by a controller for controlling the medical apparatus comprising a magnetic resonance imaging system and according to an embodiment of the invention. Execution of the instructions causes the processor to receive target data descriptive of the location of a target zone within the subject. Execution of the instructions further causes the processor to individually vibrate each of the multiple transducers using the controller. Execution of the instructions further causes the processor to acquire first magnetic resonance data during the vibration of each of the multiple transducers using the first pulse sequence.

Execution of the instructions further causes the processor to calculate a vibration map for each of the multiple transducers using the first magnetic resonance data. The vibration map is descriptive of the phase and shear strain value of vibrations caused by each of the multiple transducers within the subject. Execution of the instructions further causes the processor to calculate transducer control data to control the multiple transducers to cause a shear strain value of at least a first predetermined value within at least part of the target zone and less than a second predetermined value outside of the target zone using the vibration map for each of the multiple transducers. Execution of the instructions further causes the processor to control the multiple transducers with the transducer control data using the controller. The advantages of this have been previously discussed.

In another aspect the invention provides for a method of treating cells of a subject using the medical apparatus comprising at least one transducer with a vibrating surface. The transducer further comprises an applicator for attaching the vibrating surface to an outer surface of the subject. The transducer is operable to vibrate at a frequency between 10 Hz and 1000 Hz. The method comprises the step of applying the at least one transducer to an external surface of the subject. The method further comprises the step of controlling the at least one transducer to vibrate for greater than a predetermined period of time to treat the cells. The predetermined time is greater than 1 hour. The advantages of this method have been previously discussed within the context of the medical apparatus.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which:

FIG. 6 illustrates an example of a transducer belt;
and
FIG. 7 illustrates a magnetic resonance imaging system.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
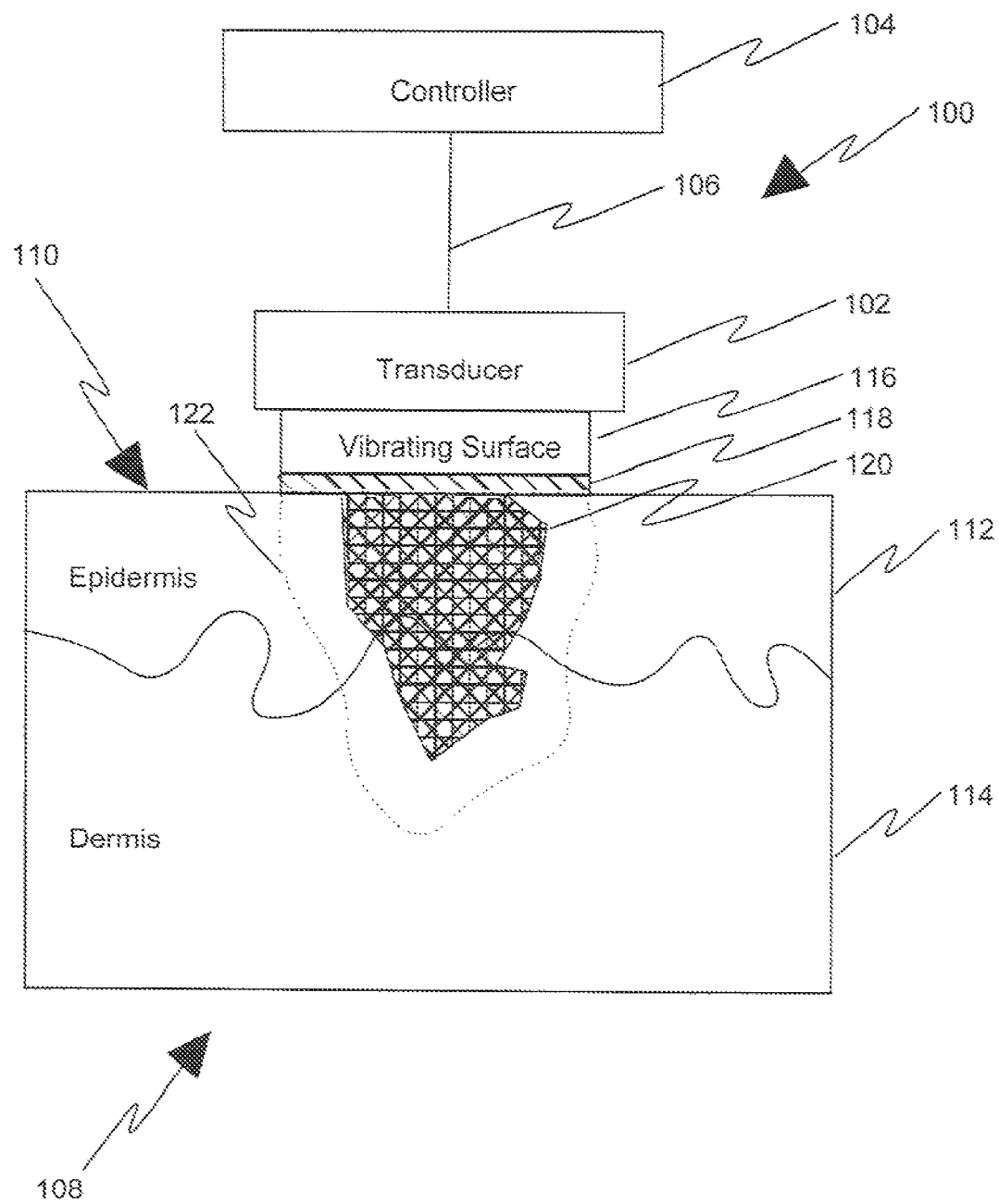
FIG. 1 illustrates an example of a medical apparatus.

FIG. 1 shows an example of a medical apparatus 100. The medical apparatus 100 comprises a transducer 102 and a controller 104 that are connected by connection 106. The transducer 102 could be for example but is not limited to a piezo transducer, a magnetic transducer, and a pneumatic transducer. The connection 106 between the controller 104 and the transducer 102 is dependent upon the type of transducer 102. The controller 104 causes the transducer 102 to actuate via the connection 106. A subject 108 in the form of a section of skin is also visible. The subject 108 has an outer surface 110. The cross-section of the subject 108 is a cross-section of skin and the epidermis 112 and the dermis 114 are visible. The transducer 102 has a vibrating surface 116 that is attached to the outer surface 110 by an adhesive layer 118. The adhesive layer 118 functions as an applicator for attaching the vibrating surface to the outer surface of the subject 108. A melanoma 120 or skin cancer is visible within the cross-section of the subject 108. It can be seen that the melanoma 120 extends from the epidermis 112 into the dermis 114.

The frequency and amplitude of the vibrations for the transducer 116 are chosen such that the region inside the dashed line 122 has a sufficient shear strain that a mechanotransduction effect such as apoptosis is induced in this region. A physician or other healthcare professional can position the transducer 102 over the melanoma 120 using its visual appearance. The controller 104 can then be set to vibrate the vibrating surface 116 sufficiently strong and for long enough duration to induce the mechanotransduction effect.

Figure 2A:
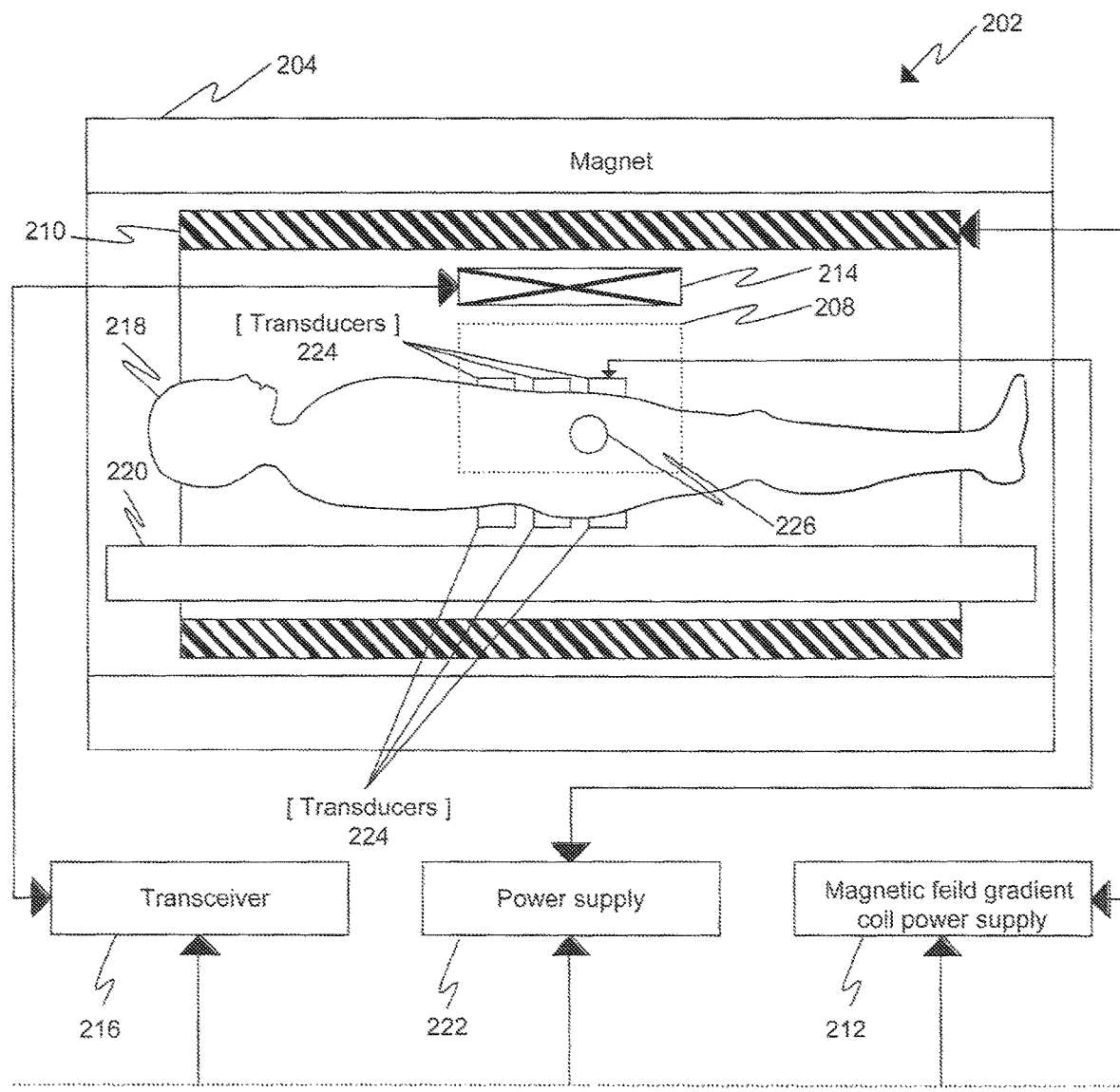
FIG. 2 illustrates a further example of a medical apparatus.
Figure 2B:
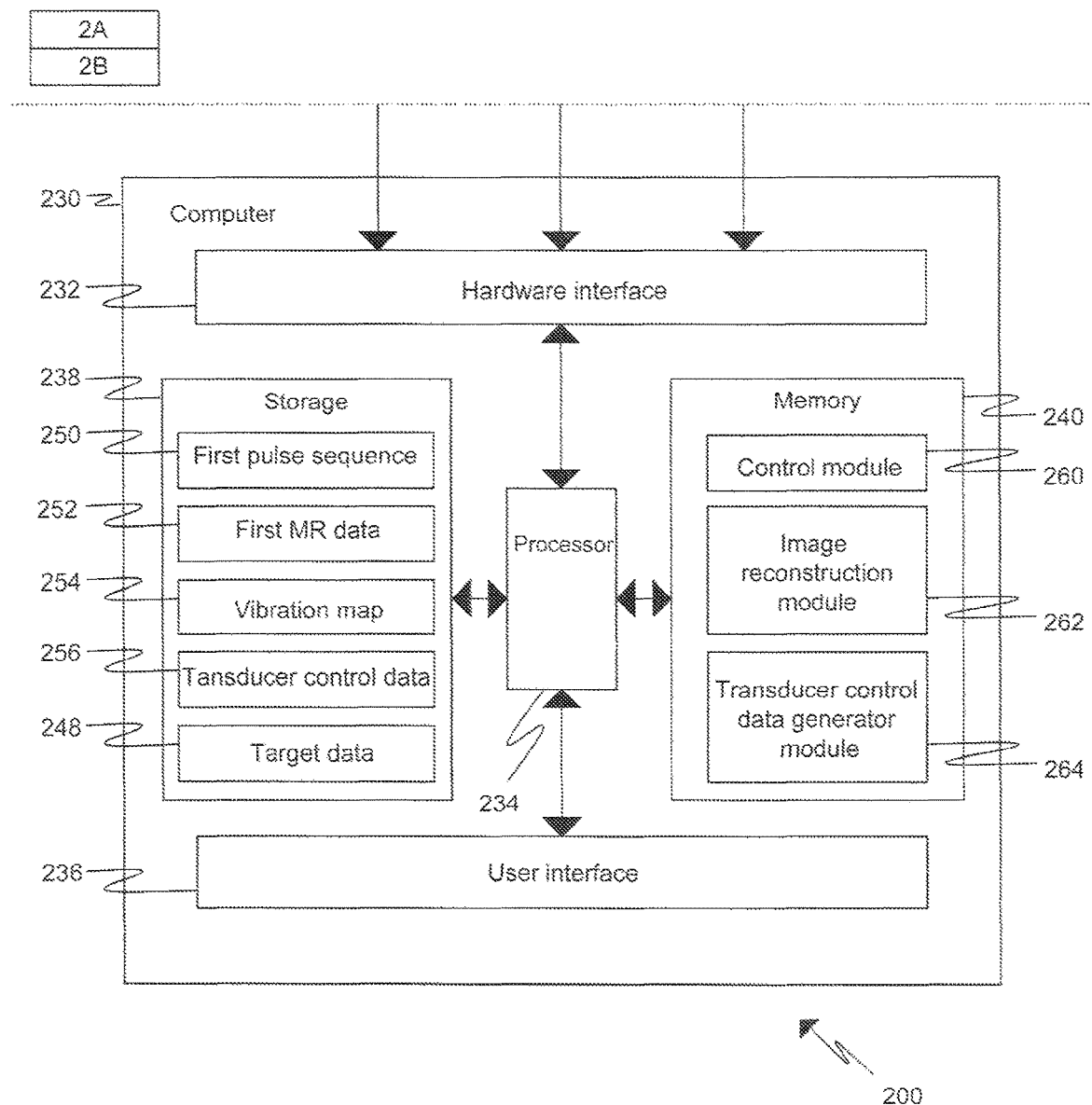

FIG. 2 shows an example of a medical apparatus 200. The medical apparatus comprises a magnetic resonance imaging system 202. The magnetic resonance imaging system 202 comprises a magnet 204. The magnet 204 is a superconducting cylindrical type magnet 204 with a bore 206 through it. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 206 of the cylindrical magnet 204 there is an imaging zone 208 where the magnetic field is strong and uniform enough to perform magnetic resonance imaging.

Within the bore 206 of the magnet there is also a set of magnetic field gradient coils 210 which is used for acquisition of magnetic resonance data to spatially encode magnetic spins within the imaging zone 208 of the magnet 204. The magnetic field gradient coils 210 connected to a magnetic field gradient coil power supply 212. The magnetic field gradient coils 210 are intended to be representative. Typically magnetic field gradient coils 210 contain three separate sets of coils for spatially encoding in three orthogonal spatial directions. A magnetic field gradient power supply supplies current to the magnetic field gradient coils. The current supplied to the magnetic field gradient coils 210 is controlled as a function of time and may be ramped or pulsed.

Adjacent to the imaging zone 208 is a radio-frequency coil 214 for manipulating the orientations of magnetic spins within the imaging zone 208 and for receiving radio transmissions from spins also within the imaging zone 208. The radio frequency antenna may contain multiple coil elements. The radio frequency antenna may also be referred to as a channel or antenna. The radio-frequency coil 214 is connected to a radio frequency transceiver 216. The radio-frequency coil 214 and radio frequency transceiver 216 may be replaced by separate transmit and receive coils and a separate transmitter and receiver. It is understood that the radio-frequency coil 214 and the radio frequency transceiver 216 are representative. The radio-frequency coil 214 is intended to also represent a dedicated transmit antenna and a dedicated receive antenna. Likewise the transceiver 216 may also represent a separate transmitter and receivers. The radio-frequency coil 214 may also have multiple receive/transmit elements and the radio frequency transceiver 216 may have multiple receive/transmit channels.

The medical apparatus 200 further comprises a power supply 222 connected to a number of transducers 224 affixed to an outer surface of a subject 218. The phase, amplitude and/or frequency of the vibrations of the transducers 224 can be controlled to concentrate the shear waves within the target volume 226. Target zone 226 is shown as being within the subject 218 and within the imaging zone 208. The transceiver 216, the magnetic field gradient coil power supply, and the power supply 222 are shown as being connected to the hardware interface 232 of a computer system 230. It should be noted that in some examples the subject support 220, the subject 218, the transducers 214 and the power supply 222 can be removed from the magnetic resonance imaging system 202 and moved to a location remote to the bore 206 of the magnet 204. This may enable another subject 218 to be placed into the magnetic resonance imaging system 202.

The computer storage 238 is shown as containing a first pulse sequence 250. The first pulse sequence is a pulse sequence which causes the magnetic resonance imaging system 202 to perform a motion sensitive magnetic resonance imaging method, that is to say a method which is able to detect or measure motion within the subject 218. The computer storage 238 is shown as further containing first magnetic resonance data 252 that was acquired using the first pulse sequence 250. The computer storage 238 is shown as further containing a vibration map 254 that was reconstructed from the first magnetic resonance data 252. The vibration map 254 is a vibration map for each of the transducers 224 or groups of transducers. The first magnetic resonance data 252 contains data descriptive of the vibrations for individual transducers 224 or groups of transducers 224. The computer storage 238 is further shown as containing transducer control data 256 which is data which enables the processor 234 to control the power supply 222 to control the amplitude and/or phase and/or frequency of the individual transducers 224 or groups of transducers 224.

The computer memory 240 is shown as containing a control module 260. The control module contains computer-executable code which enables the processor 234 to control the operation and function of the medical apparatus 200. The computer storage 240 is further shown as containing an image reconstruction module 262. The image reconstruction module 262 enables the processor 234 to reconstruct first magnetic resonance data 252 into for example the vibration map 254 and if the first magnetic resonance data comprises image data such as proton density enables the processor 234 to reconstruct magnetic resonance images. The computer memory 240 is further shown as containing a transducer control data generation module 264. The transducer control data generation module 264 is able to reconstruct or deduce the correct transducer control data 256 commands for controlling the transducers 224 to target the target zone 226 using the vibration maps 254.

The computer storage 238 is further shown as containing target data 248. The target data is descriptive of the location of the target zone 226. The transducer control data generation module 264 may use the target data 248 to properly construct the transducer control data 256.

Figure 3A:
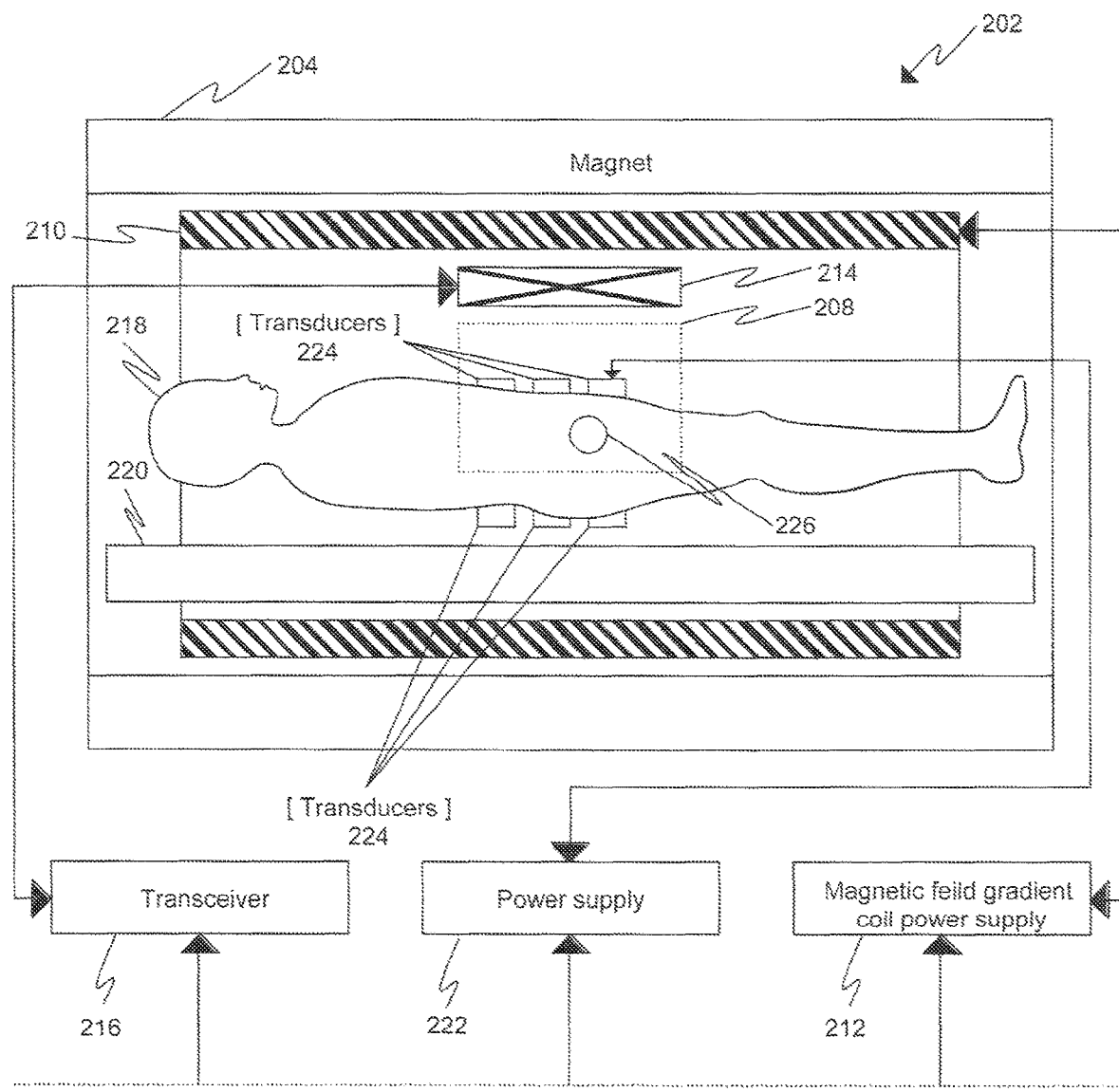
FIG. 3 illustrates a further example of a medical apparatus.
Figure 3B:
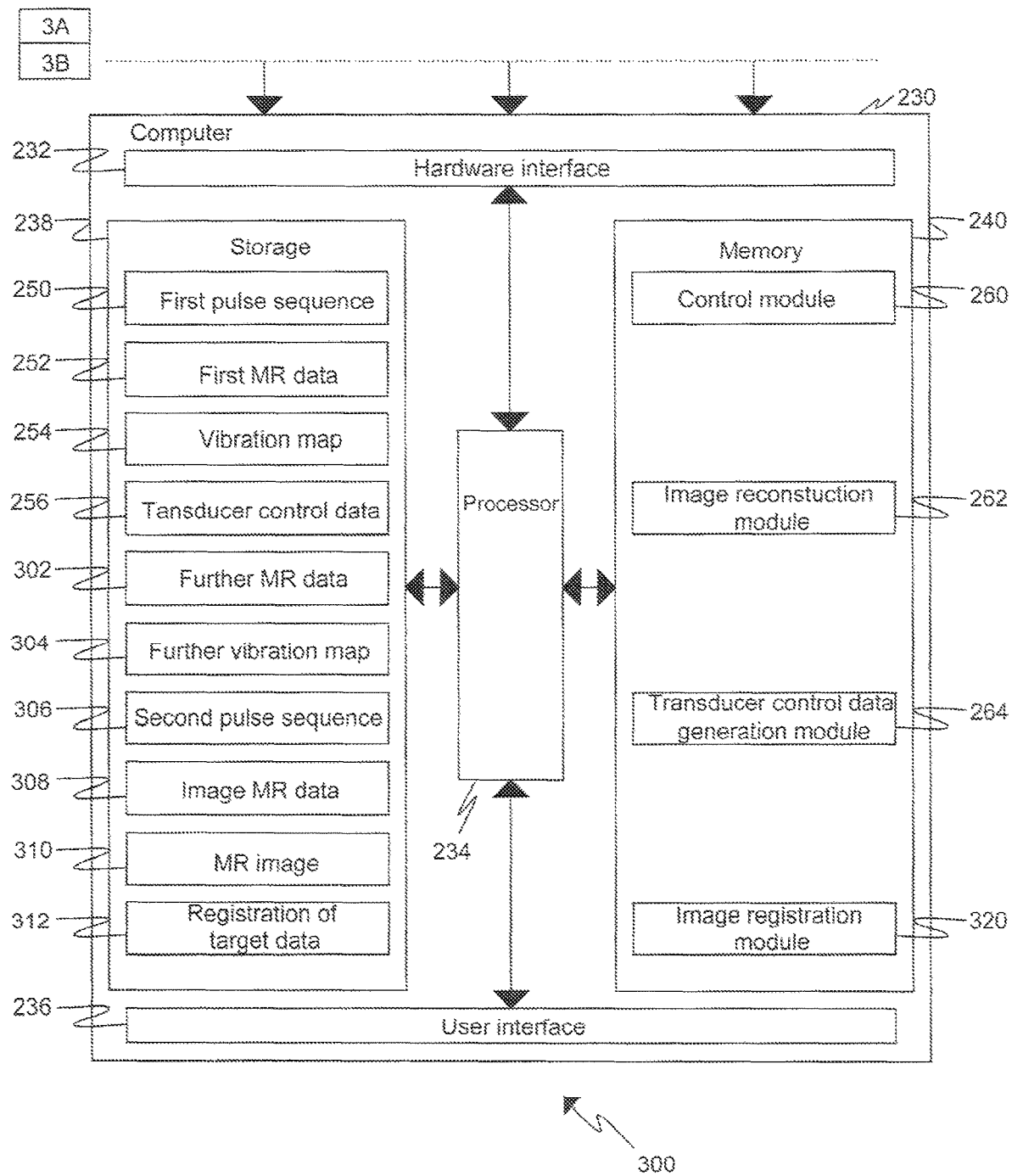

FIG. 3 shows a medical apparatus that is similar to the medical apparatus shown in FIG. 2 with additional functionality. The computer storage 238 is shown as additionally containing further magnetic resonance data. The further magnetic resonance data 302 was acquired using the first pulse sequence 250. The computer storage 238 is shown as containing a further vibration map 304 that was reconstructed using the image reconstruction module 262. The further vibration map 304 may be used to determine if the target zone 226 is correctly targeted by the transducers 224 or may also be used as input to the transducer control data generation module 264 to correct the transducer control data 256. The computer storage 238 is further shown as containing a second pulse sequence 306. The second pulse sequence 306 contains a pulse sequence that may be used for acquiring imaging magnetic resonance data.

The computer storage 238 is further shown as containing image magnetic resonance data that was acquired 308 using the second pulse sequence 306. The computer storage 238 is shown as further containing the magnetic resonance image 310 that was reconstructed from the image magnetic resonance data 308 using the image reconstruction module 262. The computer storage 238 is shown as further containing a registration of the target data 312 that was made using the target data 248 and the magnetic resonance image 310 as input to an image registration module 320. The image registration module 320 is shown as being stored in the computer memory 240. The contents of the computer memory 240 may also be stored in the computer storage 238 and vice versa.

Figure 4:
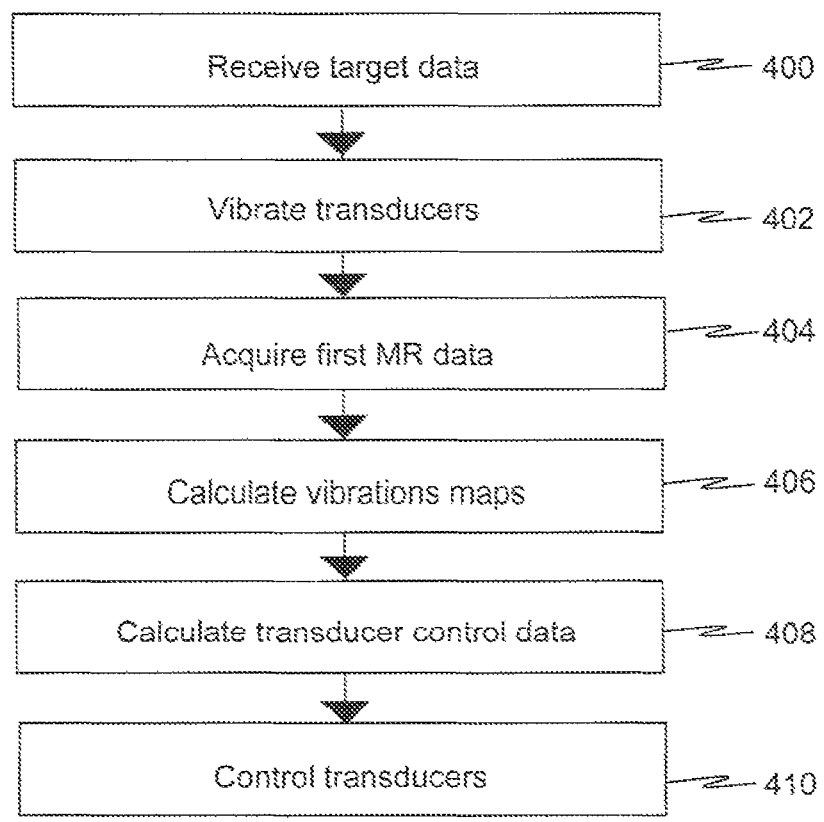
FIG. 4 shows a flow chart which illustrates a method.

FIG. 4 shows a flowchart which illustrates a method which is suitable for operating the medical apparatus 200 of FIG. 2 or the medical apparatus 300 of FIG. 3. First in step 400 target data which is descriptive of the location of a target zone within the subject is received. Next in step 402 each of the multiple transducers using the controller are individually vibrated. Alternatively groups of multiple transducers may also be vibrated. In step 404 first magnetic resonance data is acquired during the vibration of each of the multiple transducers using a first pulse sequence. Next in step 406 a vibration map is calculated for each of the multiple transducers using the first magnetic resonance data. This also applies to groups of transducers that are vibrated at the same time. The vibration map is descriptive of the phase and shear strain value of vibrations caused by each of the multiple transducers within the subject. Next in step 408 transducer control data is calculated to control the multiple transducers to cause a shear strain value of at least a first predetermined value within at least a part of the target zone and less than a second predetermined value outside of the target zone using a vibration map for each of the multiple transducers. And finally in step 410 the multiple transducers are controlled within the transducer control data using the controller.

Figure 5:
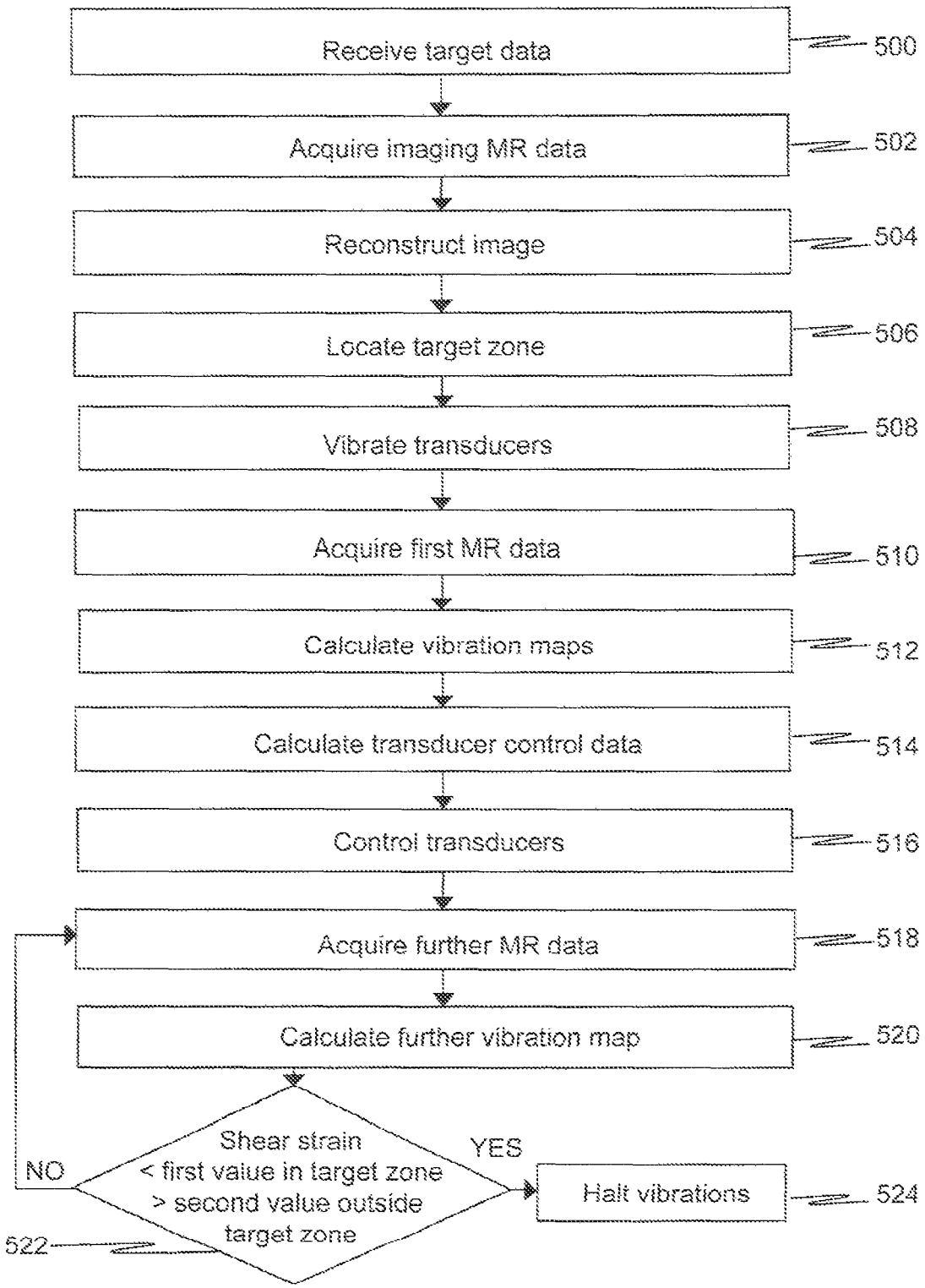
FIG. 5 shows a flow chart which illustrates a further example of a method.

FIG. 5 shows a flowchart illustrating a method suitable for controlling the medical apparatus 300 shown in FIG. 3. First in step 500 target data is received which is descriptive of the location of the target zone within the subject. Next in step 502 image or imaging magnetic resonance data is acquired using the second pulse sequence. Then in step 504 an image is reconstructed using the imaging magnetic resonance data. In step 506 the target zone is located within the image using an image recognition module. This may be done to construct the image registration of the target data. Then in step 508 each of the multiple transducers are individually vibrated using the controller.

In step 510 first magnetic resonance data is acquired during the vibration of each of the multiple transducers using the first pulse sequence. Then in step 512 a vibration map is calculated for each of the multiple transducers using the first magnetic resonance data. The vibration map is descriptive of the phase and shear strain value of vibrations caused by each of the multiple transducers in the subject. Then in step 514 transducer control data is calculated to control the multiple transducers to cause a shear strain value of at least a first predetermined value within at least a part of the target zone and less than a second predetermined value outside of the target zone using the vibration map for each of the multiple transducers. Then next in step 516 multiple transducers are controlled with transducer control data using the controller. This causes the transducers to vibrate and cause shear strain within the target zone.

Next in step 518 further magnetic resonance data is acquired during the time when the transducers are vibrating. The further magnetic resonance data is used in step 520 to calculate a further vibration map using the further magnetic resonance data. 522 is a decision box. In decision box 522 the question is asked if the shear strain value is below the first predetermined value within at least a part of the target zone and/or is greater than the second predetermined value outside of the target zone. If the questions is answered is yes then step 524 is performed next. In step 524 the vibrations are halted.

If the question is answered with "no" then the shear strain values are at least above the first predetermined value within the target zone and/or is not greater than the second predetermined value outside the target zone then the transducers are allowed to continue to vibrate. In some examples this may form a closed control loop and the method may return to step 518 periodically. In other embodiments or examples it is assumed that for the duration of the vibration of the transducers the shear strain value will remain relatively constant within the subject and it is not necessary to further monitor it.

FIG. 6 is an example of a transducer belt 600. The transducer belt is a plastic belt which functions as an applicator for attaching the transducers to the outer surface of the subject. A number of transducers 224 are shown as being attached to the belt 600. There is a cable 602 for attaching to the power supply 222 of FIG. 2. The cable may be bundled or connected together in a sheath for tidiness but in this case each transducer is able to be driven separately. The cable 602 provides each individual transducer with a drive signal.

FIG. 7 shows a three-dimensional view of a magnetic resonance imaging system 202. The subject 108 is reposing on a subject support 220 within the bore 206 of the magnet 204. Transducers 224 are attached to the subject 108 using a belt 600 as is shown in FIG. 6. However, the belt 600 is not visible in this picture.

Examples may apply shear stress to in-vivo (cancerous) cells in order to induce cell-death. The shear stress by transverse shear waves with a frequency of around 100 Hz, is induced by a multiplicity of actuators and attains maximum shear strain values of the order of 5%. The phases/amplitudes of these actuators may be tuned in order to focus the shear waves onto the area of the pathology (tumor for instance). This tuning/focusing is guided by the use of MR, most notably MR-Elastography, which can image the actual degree of shear motion patient specifically. Mind that normal maximum shear strain levels typically used in MR-Elastography are of the order of 0.1%, hence a factor 10 lower and applied over a much shorter time.

There are many potential ways of killing unwanted (e.g. malignant) cells within the human body. One way is by "brute force", e.g. by applying an overdose of ionizing radiation (RT) or by heating tissues sufficiently to induce necrotic coagulation (e.g. by HIFU).

Another mechanism is for instance programmed cell death or apoptosis: trigger a cell into the process of terminating itself. Cells can be triggered into apoptosis by applying mechanical shear stress. This was already known, but an inventive insight is that this apoptosis can also be invoked by a cyclical shear stress i.e. vibration.

Experiments show that vibrations (tests have run at around 100 Hz) of sufficient amplitude and applied during a sufficiently long duration can indeed cause a significant amount of cell apoptosis. They are also able to induce cell-kill via other pathways (direct necrosis for instance) which are currently investigated.

Apoptosis may be induced by applying vibrational shear stress to a subject in order to trigger to specific cells within that body a certain mechanical signal which leads to cell-kill. Various mechanisms are possible, one of which we already investigated is apoptosis. This concept may be applied in order to locally kill cancer cells for instance. Furthermore, the idea is to do this via a multiplicity (envisaged are around 100) of actuators wrapped around the body. The amplitudes and phases of these actuators are arranged in order to have maximum amplitude of shear stress within a region of interest and minimal amplitude elsewhere. Thereby the potential lack of specificity for killing a certain cell type can be overcome via the fact that the necessary level of maximum shear strain is attained only locally and nowhere else.

Since a human body or other subject is a "difficult" medium to model acoustic waves at low frequency (1-1000 Hz), a further idea is to use MR in order to detect the actual transmit pattern of each of the actuators. This is feasible with MRI). In fact, MRI can generate a map of the amplitude and phase of each of the vibration sources but also of the combined effect of each of the actuators or set of actuators. This MRI-mapping allows to properly set phases and amplitudes of the actuators for focussing.

Additional Elements

The technology for the actuators or transducers may be piezo-electric. The envisaged frequency is around 1-1000 Hz. Probably, for much lower frequencies, the treatment may take longer, and transverse waves (or shear waves) penetrate the human body less for much higher frequencies The idea is to use MR to map the actuator-intensity patterns. For example, this mapping may be done by using lower power, or less time, than with the actual treatment. In other examples this may be done at full power.

Since it is likely that treatment would take a substantial amount of vibration-time, e.g. more than an hour, the system may be designed such that the patient+actuator system is withdrawn from the MR device once the focussing has been established.

When performing beamforming, the deposited power at the focal point will, in a first approximation, depend upon the number of transducers. Hence, increasing the number of transducers will enable to obtain 5% strain at the focused area while dividing the power deposited by each individual transducer to values well below the threshold. As a design principle, one can favor belt designs with a higher number of transducers (to the obvious limit that the transducer must not be so small as to have a penetrating distance insufficient to reach the desired focal point).

Shear waves may be selectively applied to tumors via the familiar concepts of focussing. This is technologically very advanced thanks to developments generated through the HIFU technology. There are no major physical constraints in applying these well-known concepts to lower frequency ranges. The dramatic changes undergone by cancerous cells relative to healthy cells may even provide a type of sensitization to mechanical shear.

In the following, we provide proof of concept that mechanical shear may induce cell death via apoptosis, in a process involving dramatically reduced energy deposition levels relative to for instance HIFU techniques.

Shear-Induced Cell Injury Assay
Material and Methods

Cell experiments were carried out on DHD/K12 rat colonic carcinoma cells, chosen for their robust metastatic phenotype in vitro. All cell culture experiments were carried out in DMEM medium supplemented with 2 mM glutamine and 10% fetal bovine serum. Third passage DHD/K12 cells were plated at a density of 250000, 500000, 750000 or 1000000 cells per well in two standard cell culture 24 wells plate (1.86 cm$^2$ flat-bottom wells, TPP, Switzerland). One of the plates was modified to fit the mount of a specially designed plate holder with a slot for an acoustic shaker.

Alternate Rigid Metal Linkage

When in use, the acoustic shaker was encased in an impermeable sterilizable pouch to prevent damage from the water vapor found in cell culture incubators. The control plate was placed in a different incubator to avoid stray vibrations from the vibrating setup. The test plate was subjected to 1.5 $V_{ptp}$ vibrations (~10 μm amplitude) at 90 Hz for 5 hours in otherwise normal growth conditions (5% $CO_2$, 37.5° C.). Based on numerical simulations, this frequency was found to correspond to a vibration resonance condition for the cell culture plate.

Numerical simulations: estimation of the resonance frequency on a 24-wells plate. A first resonance frequency was found at 90 Hz.

Before and after the 5 hours, an exhaustive cell count was performed. Cells from the supernatant culture medium were counted, as well as cells from the monolayer attached to the surface of the cell culture plate. A trypan blue cell viability assay was performed on both cell populations (supernatant and cell monolayer). For the cells in the monolayer, cells were first rinsed with phosphate buffered saline, then detached from the monolayer by trypsinization (6 minutes incubation at 37° C. in 0.25% trypsin/EDTA). Trypsinization was stopped by diluting the suspension with room temperature, calcium-containing DHDK12 cell culture medium. Ten μl of cell suspensions (from supernatant and monolayer) were diluted in an equal volume of trypan blue (sigma), and the resulting suspension was layered on a Malassez cell and allowed to incubate for 1 min. Exhaustive cell counts were performed on 1 mm$^3$ of the trypan blue mixture using the grid of the Malassez cell. Transparent and blue cells were inventoried, and counted as live or dead cells, respectively.

Cell growth rates were evaluated in response to various durations of the exposure to vibrations. After exposure to 4, 7 or 21 hours of vibration, cells were detached from the plate using conventional techniques. A cellular count was made and a fixed number of cells was seeded on a control plate. Cellular count were performed daily thereafter for 4 days. Growth rates were estimated by using a logarithmic growth model with no lag time.

Apoptosis was estimated by evaluating the levels of caspase-3. Caspase-3 is an effector caspase, and is typically found activated in late stage apoptosis, when the cell is engaged towards death. Hence, although it is not specific of any one apoptosis pathway, because of its downstream position in the apoptosis pathway, it represents an unambiguous indicator that apoptosis is indeed taking place. Caspase-3 levels were estimated via western blotting, using beta-actin as total protein control.

Results

In control conditions, cultured DHDK12 cells were found to be very adhesive, as little to no cells was found in the culture medium. The vibrating condition yielded some cellular detachment, as evidenced by the presence of 4000 cells/ml in the supernatant of the vibrating plate (zero for the still plate). The number of cells in the sampled suspension was too low for an accurate determination of the percent viability of this cell population. In the population of cells adhering to the culture plate, more cells were found to uptake the trypan blue dye in the vibrating plate than in the still plate.

Interestingly, the overall number of cells was found to increase slightly in the still plate (as expected from normal cellular growth) but decreased in the vibrated plate. The fact that these missing cells were not found in the supernatant may be indicative of cellular lysis having occurred throughout the experiment. The percentage of dead cells was found to increase substantially between the still plate and the plate having undergone vibrations, see the following table:

|  | timepoint | Cell count ($\times 10^3$ cells/mL) | Percent dead cells (%) |
| --- | --- | --- | --- |
| Still plate | t0 | 517.0 | 2.9 |
|  | t0 + 5 hours, no vibration | 557.4 | 4.5 |
| Vibrated plate | t0 | 581.7 | 5.2 |
|  | t0 + 5 hours, 90 Hz vibration | 459.6 | 22.3 |

Growth rate of cells exposed to 4, 7 or 21 hours of vibration (vs. control, non vibrated cells). Regardless of the duration of the exposure to vibration, the vibrated cells always display lower growth rates than control cells.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or

LIST OF REFERENCE NUMERALS 100 medical apparatus
102 transducer
104 controller
106 connection
108 subject
110 outer surface
112 epidermis
114 dermis
116 vibrating surface
118 adhesive layer
120 melanoma
122 target region
200 medical apparatus
202 magnetic resonance imaging system
204 magnet
206 bore of magnet
208 imaging zone
210 magnetic field gradient coils
212 magnetic field gradient coil power supply
214 radio-frequency coil
216 transceiver
218 subject
220 subject support
222 power supply
224 transducer
226 target zone
230 computer system
232 hardware interface
234 processor
236 user interface
238 computer storage
240 computer memory
248 target data
250 first pulse sequence
252 first magnetic resonance data
254 vibration map
256 transducer control data
260 control module
262 image reconstruction module
264 transducer control data generation module
300 medical apparatus
302 further magnetic resonance data
304 further vibration map
306 second pulse sequence
308 image magnetic resonance data
310 magnetic resonance image
312 registration of target data
320 image registration module
600 transducer belt

The invention claimed is:

1. A medical apparatus for treating cells of a subject comprising at least one transducer with a vibrating surface, wherein the transducer further comprises an applicator for attaching the vibrating surface to an outer surface of the subject, wherein the transducer is operable to vibrate at a frequency between 10 Hz and 1000 Hz, wherein the medical apparatus further comprises a controller for controlling the vibration of the transducer, wherein the controller is operable for causing the transducer to vibrate for greater than a predetermined period of time for treating the cells, wherein the predetermined period of time is greater than one hour, wherein the controller controls the vibration to provide a shear strain value greater than a first predetermined value in a target zone and shear strain value less than a second predetermined value outside the target zone, and wherein the second predetermined value is less than the first predetermined value, wherein the controller is operable for controlling at least one of a vibrational phase or amplitude of the at least one transducer, wherein the controller comprises a processor, wherein the medical apparatus further comprises:
a memory for storing machine executable instructions and a first pulse sequence, wherein the first pulse sequence is a motion sensitive pulse sequence, wherein execution of the instructions causes the processor to:
receive target data descriptive of the location of a target zone within the subject;
individually vibrate the at least one transducers using the controller;
acquire first magnetic resonance data during the vibration of at least one transducer using the first pulse sequence;
calculate a vibration map for the at least one transducer using the first magnetic resonance data, wherein the vibration map is descriptive of the phase and shear strain value of vibrations caused by the at least one transducer within the subject;
calculate transducer control data to control the at least one transducer to cause a shear strain value of at least a first predetermined value within at least part of the target zone and a shear strain value less than a second predetermined value outside of the target zone using the vibration map for the at least one transducer; and
control the at least one transducer with the transducer control data using the controller.

2. The medical apparatus of claim 1, wherein execution of the instructions further causes the processor to:
acquire further magnetic resonance data during control of the at least one transducer with the transducer control data using a magnetic resonance imaging system with the first pulse sequence;
calculate a further vibration map using the further magnetic resonance data; and
halt vibration of the at least one transducer if the shear strain value is below the first predetermined value within at least part of the target zone or is greater than the second predetermined value outside of the target zone.

3. The medical apparatus of claim 1, wherein the memory stores a second pulse sequence, wherein the second pulse sequence is an imaging pulse sequence, wherein execution of the instructions further causes the processor to:
acquire image magnetic resonance data of the subject using the magnetic resonance imaging system using the second pulse sequence;
reconstruct an image using the image magnetic resonance data; and
locate the target zone within the image using an image recognition module.

4. The medical apparatus of claim 1, wherein the at least one transducer comprises multiple transducers, and the controller is operable for individually adjusting the vibration frequency of the multiple transducers, wherein execution of the instructions further causes the processor to repeat the individual vibration of the multiple transducers using the controller and acquisition of the first magnetic resonance data using multiple transducer frequencies, wherein the vibration map is a multi-frequency vibration map, wherein calculating the transducer control data comprises selecting the frequency for the multiple transducers.

5. The medical apparatus of claim 1, wherein the at least one transducer comprises multiple transducers, and the controller is operable for individually adjusting, the vibrational amplitude and phase of the multiple transducers, and wherein calculating the transducer control data comprises individually selecting a vibrational amplitude and phase for the multiple transducers.

6. The medical apparatus of claim 1, wherein the magnetic resonance imaging system comprises a magnet for generating a main magnetic field, wherein the at least one transducer are operable for functioning within and outside of the main magnetic field.

7. The medical apparatus of claim 1, wherein the medical instrument comprises a subject support, wherein the subject support is operable for removing the subject, the controller, and the at least one transducer from the magnetic resonance imaging system during the predetermined period of time.

8. The medical apparatus of claim 1, wherein the at least one transducer are electromagnetically driven transducers.

9. The medical apparatus of claim 1, wherein the first predetermined value is greater than or equal to any one of the following: 0.1%, 1%, 2%, and 5%; and wherein the second predetermined value is less than or equal to 0.05%.

10. The medical apparatus of claim 1, wherein the at least one transducer is a single transducer, wherein the applicator is operable for attaching the vibrating surface to skin, and wherein the vibrating surface has a surface area less than 0.25 square centimeters.

11. The medical apparatus of claim 10, wherein the frequency is between 200 and 1000 Hz.

12. The medical apparatus of claim 1, wherein the predetermined period of time is greater than 1.5 hours, the shear strain in the target zone is sufficient to cause apoptosis, and the shear strain outside of the target zone is not sufficient to cause apoptosis.

13. A computer program product comprising machine executable instructions for execution by a controller for controlling a medical apparatus for treating cells of a subject, wherein execution of the instructions causes the processor to:
receive target data descriptive of the location of a target zone within the subject;
individually vibrate a plurality of transducers using the controller;
acquire first magnetic resonance data during the vibration of the plurality of transducers using the first pulse sequence and a magnetic resonance imaging system;
calculate a vibration map for the plurality of transducers using the first magnetic resonance data, wherein the vibration map is descriptive of the phase and shear strain value of vibrations caused by individually vibrating the plurality of transducers within the subject;
calculate transducer control data to control the plurality of transducers to cause a shear strain value of at least a first predetermined value within at least part of the target zone and less than a second predetermined value outside of the target zone using the vibration map for the plurality of transducers; and
control the plurality of transducers with the transducer control data using the controller.

14. The computer program product of claim 13, wherein execution of the instructions further causes the processor to:
acquire further magnetic resonance data during control of the plural transducers with the transducer control data using the magnetic resonance imaging system with the first pulse sequence;
calculate a further vibration map using the further magnetic resonance data; and
halt vibration of the plurality of transducers if the shear strain value is below the first predetermined value within at least part of the target zone or is greater than the second predetermined value outside of the target zone.

15. A method for treating cells of a subject using a medical apparatus comprising at least one transducer with a vibrating surface, wherein the transducer further comprises an applicator for attaching the vibrating surface to an outer surface of the subject, wherein the transducer is operable to vibrate at a frequency between 10 Hz and 1000 Hz, wherein the method comprises the steps of:
applying the at least one transducer to an external surface of the subject,
controlling the at least one transducer to vibrate for greater than a predetermined period of time to treat the cells, wherein the predetermined time is greater than one hour and wherein the vibration provides a shear strain value greater than a first predetermined value in a target zone and shear strain value less than a second predetermined value outside the target zone wherein the second predetermined value is less than the first predetermine value;
receiving target data descriptive of the location of the target zone within the subject;
individually vibrating the at least one transducers using the controller;
acquiring first magnetic resonance data during the vibration of the at least one transducer using a first pulse sequence;
calculating a vibration map for the at least one transducer using the first magnetic resonance data, wherein the vibration map is descriptive of the phase and shear strain value of vibrations caused by the at least one transducer within the subject;
calculate transducer control data to control the at least one transducer to cause a shear strain value of at least a first predetermined value within at least part of the target zone and less than a second predetermined value outside of the target zone using the vibration map for the at least one transducer; and
control the at least one transducer with the transducer control data using the controller.

16. The method of claim 15, further comprising the steps of:
acquiring further magnetic resonance data during control of the at least one transducer with the transducer control data using a magnetic resonance imaging system with the first pulse sequence;
calculate a further vibration map using the further magnetic resonance data; and
halt vibration of the at least one transducer if the shear strain value is below the first predetermined value within at least part of the target zone or is greater than the second predetermined value outside of the target zone.

17. The method of claim 15, wherein the at least one transducer comprises multiple transducers, the method further comprising the steps of:
Individually adjusting the vibration frequency of the multiple transducers, repeating the individual vibration of the multiple transducers using the controller, and acquiring the first magnetic resonance data using multiple transducer frequencies, wherein the vibration map is a multi-frequency vibration map, wherein calculating the transducer control data comprises selecting the frequency for the multiple transducers.

18. The method of claim 15, wherein the at least one transducer comprises multiple transducers, the method further comprising the step of:

Individually adjusting the vibrational amplitude and phase of the multiple transducers, wherein calculating the transducer control data comprises individually selecting a vibrational amplitude and phase for the multiple transducers.

* * * * *